US012014281B2

(12) United States Patent
Dehan et al.

(10) Patent No.: US 12,014,281 B2
(45) Date of Patent: Jun. 18, 2024

(54) AUTOMATIC PROCESSING OF ELECTRONIC FILES TO IDENTIFY GENETIC VARIANTS

(71) Applicant: Merative US L.P., Ann Arbor, MI (US)

(72) Inventors: Elinor Dehan, Haniel (IL); Bhuvan Sharma, Belmont, MA (US); Claudia S. Huettner, Jamaica Plain, MA (US); Kirk Alan Beaty, Goldens Bridge, NY (US); Shang Xue, Santa Clara, CA (US); Himanshu Sharma, Cambridge, MA (US)

( * ) Notice: Subject to any disclaimer, the term of this patent is extended or adjusted under 35 U.S.C. 154(b) by 882 days.

(21) Appl. No.: 16/952,667

(22) Filed: Nov. 19, 2020

(65) Prior Publication Data

US 2022/0156597 A1    May 19, 2022

(51) Int. Cl.
| G06N 3/126 | (2023.01) |
| G16H 10/20 | (2018.01) |
| G16H 10/40 | (2018.01) |
| G16H 15/00 | (2018.01) |
| G16H 50/70 | (2018.01) |
| G16H 70/60 | (2018.01) |

(52) U.S. Cl.
CPC ............ *G06N 3/126* (2013.01); *G16H 10/20* (2018.01); *G16H 10/40* (2018.01); *G16H 15/00* (2018.01); *G16H 50/70* (2018.01); *G16H 70/60* (2018.01)

(58) Field of Classification Search
None
See application file for complete search history.

(56) References Cited

U.S. PATENT DOCUMENTS

| 10,185,803 | B2 | 1/2019 | Frey | |
| 10,235,496 | B2 | 3/2019 | Torkamini | |
| 2014/0359422 | A1* | 12/2014 | Bassett, Jr. | ............ G16B 20/00 |
| | | | | 707/754 |
| 2015/0363559 | A1 | 12/2015 | Jackson et al. | |
| 2016/0078472 | A1* | 3/2016 | Asur | ................ G06Q 30/0245 |
| | | | | 705/14.44 |
| 2016/0224730 | A1 | 8/2016 | Yu et al. | |
| 2016/0357903 | A1* | 12/2016 | Shendure | ............... G06N 20/00 |
| 2016/0364522 | A1* | 12/2016 | Frey | ....................... G16B 40/20 |

(Continued)

FOREIGN PATENT DOCUMENTS

| EP | 3276517 A1 | 1/2018 |
| EP | 32765117 A1 | 1/2018 |

(Continued)

OTHER PUBLICATIONS

Neural Relation Extraction Within and Across Sentence Boundaries Author: Gupta et al. (Year: 2019).*

(Continued)

*Primary Examiner* — Mandrita Brahmachari
(74) *Attorney, Agent, or Firm* — Stephen J. Walder, Jr.

(57) ABSTRACT

A mechanism is provided for processing electronic files to identify genetic variants of a gene. Evidence of one or more genetic variants of the gene and corresponding information is extracted from a corpus of information. Each genetic variant of the one or more genetic variants is classified based on whether the genetic variant is identified as being pathogenic. Genetic variant annotation is then performed to generate a summary.

20 Claims, 5 Drawing Sheets

(56) References Cited

U.S. PATENT DOCUMENTS

| | | | |
|---|---|---|---|
| 2017/0185720 | A1 | 6/2017 | Downs et al. |
| 2019/0108309 | A1 | 4/2019 | Michelini et al. |
| 2019/0197401 | A1 | 6/2019 | Jaganathan et al. |
| 2019/0198138 | A1 | 6/2019 | Baldwin et al. |
| 2019/0354595 | A1* | 11/2019 | Sabharwal ............. G06N 3/045 |
| 2020/0005893 | A1 | 1/2020 | Huettner et al. |
| 2020/0176098 | A1 | 6/2020 | Lucas et al. |
| 2021/0343363 | A1* | 11/2021 | Yen ......................... G16B 5/20 |

FOREIGN PATENT DOCUMENTS

| | | |
|---|---|---|
| WO | WO2015/148776 A1 | 1/2015 |
| WO | WO2019/079180 A1 | 4/2019 |

OTHER PUBLICATIONS

List of IBM or Patent Applications Treated as Related (Appendix P), Mar. 29, 2021, 2 pages.

"IBM Watson for Genomics, Sample Report", Version 38.155, Analyzed on: May 23, 2018, 33 pages.

"Other Variant Based Features", NHGRI, https://research.nhgri.nih.gov/skippy/features-other.shtml, [Accessed Jun. 5, 2020], 3 pages.

"PathoMAN", https://pathoman.mskcc.org/PathoMANmethodDescription, Downloaded from the internet on Mar. 29, 2020, 4 pages.

"Sophia Genetics Presents Alamut Genova, the Latest Evolution of the Alamut Software for Genomic Variant Exploration", https://www.sophiagenetics.com/en_US/news/media-mix/details/news/sophia-genetics-presents-alamut-genova-the-latest-evolution-of-the-alamut-software-for-genomic-variant-exploration.html, Oct. 17, 2018, 3 pages.

"Splicing Prediction Module", Interactive-Biosoftware, https://www.interactive-biosoftware.com/doc/alamut-visual/2.6/splicing.html, Jun. 2020, 10 pages.

"What is Combined Annotation Dependent Depletion (CADD)?", https://cadd.gs.washington.edu/, Downloaded from the internet on Mar. 29, 2020, 2 pages.

Ellingford, Jaime M. et al., "Functional and in-silico interrogation of rare genomic variants impacting RNA splicing for the diagnosis of genomic disorders", https://www.biorxiv.org/content/10.1101/781088v1.full, Sep. 2019, 29 pages.

Jaganathan, Kishore et al., "Predicting Splicing from Primary Sequence with Deep Learning", Cell, vol. 176, Issue 3, Jan. 24, 2019, 39 pages.

Quang, Daniel et al., "DANN: a deep learning approach for annotating the pathogenicity of genetic variants", Bioinformatics, vol. 31, Issue 5, Mar. 1, 2015, 3 pages.

Sonnenburg, Soren et al., "Accurate splice site prediction using support vector machines", BMC Bioinformatics vol. 8, Article No. S7 Dec. 2007, 16 pages.

Xu, Jia et al., "Translating cancer genomics into precision medicine with artificial intelligence: applications, challenges and future perspectives", Human Genetics 138(2) Feb. 2019, 16 pages.

Lu, Zhi-Xiang et al., "Context-Dependent Robustness to 5' Splice Site Polymorphisms in Human Populations", Human Molecular Genetics, vol. 20, No. 6, 13 pages, Dec. 2010.

Ogino, Shuji et al., "Standard Mutation Nomenclature in Molecular Diagnostics", Journal of Molecular Diagnostics, vol. 9, No. 1, 6 pages, Feb. 2007.

Yeo, Gene et al., "Maximum Entropy Modeling of Short Sequence Motifs with Applications to RNA Splicing Signals", Journal of Computational Biology, vol. 11, No. 2-3, 18 pages, Nov. 2004.

Agichtein, Eugene et al., "Snowball: Extracting Relations from Large Plain-Text Collections", Proceedings of the Fifth ACM Conference on Digital Libraries, Association for Computing Machinery, pp. 85-94, Jun. 2000.

Alex, Beatrice et al., "Automating Curation Using a Natural Language Processing Pipeline", Genome Biology, 9(S2): S10, 14 pages, Sep. 2008.

Birgmeier, Johannes et al., "AVADA: Toward Automated Pathogenic Variant Evidence Retrieval Directly from the Full-Text Literature", Genetics in Medicine 22(2): 362-370, 9 pages, Aug. 2019.

Cohen, K B. et al., "Text Mining for Translational Bioinformatics", PLoS Computational Biology, Chapter 16, 9(4): article e1003044, 9 pages, Apr. 2013.

Gajendran, Varun K. et al., "An Application of Bioinformatics and Text Mining to the Discovery of Novel Genes Related to Bone Biology", Bone 40: 1378-1388, 11 pages, Jan. 2007.

Pandey, Kapil R. et al., "The Curation of Genetic Variants: Difficulties and Possible Solutions", Geonomics Proteomics & Bioinformatics, vol. 10: 317-325, 9 pages, Nov. 2012.

\* cited by examiner

AUTOMATIC PROCESSING OF ELECTRONIC FILES TO IDENTIFY GENETIC VARIANTS

BACKGROUND

The present application relates generally to an improved data processing apparatus and method and more specifically to mechanisms for automatically processing electronic files to identify genetic variants, With the increased usage of computing networks, such as the Internet, humans are currently inundated and overwhelmed with the amount of information available to them from various structured and unstructured sources. However, information gaps abound as users try to piece together what they can find that they believe to be relevant during searches for information on various subjects. To assist with such searches, recent research has been directed to generating systems which may take an input request, analyze it, and return results indicative of the most probable result to the input request. Systems provide automated mechanisms for searching through large sets of sources of content, e.g., electronic documents, and analyze them with regard to an input request to determine a result to the input request and a confidence measure as to how accurate the result is for addressing the input request.

Examples, of systems are Siri® from Apple®, Cortana® from Microsoft®, and the IBM Watson™ cognitive system available from International Business Machines (IBM®) Corporation of Armonk, New York. The IBM Watson™ system is an application of advanced natural language processing, information retrieval, knowledge representation and reasoning, and machine learning technologies to the field of open domain result identification. The IBM Watson™ system is built on IBM's technology used for hypothesis generation, massive evidence gathering, analysis, and scoring. IBM Watson™ takes an input request, analyzes it, decomposes the request into constituent parts, generates one or more hypothesis based on the decomposed request and results of a primary search of sources, performs hypothesis and evidence scoring based on a retrieval of evidence from evidence sources, performs synthesis of the one or more hypothesis, and based on trained models, performs a final merging and ranking to output a result to the input request along with a confidence measure.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system, is provided for processing electronic files to identify genetic variants of a gene. The illustrative embodiment extracts evidence of one or more genetic variants of the gene and corresponding information from the electronic files in a corpus of information. The illustrative embodiment classifies each genetic variant of the one or more genetic variants based on whether the genetic variant is identified as being pathogenic. The illustrative embodiment performs genetic variant annotation to generate a summary.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
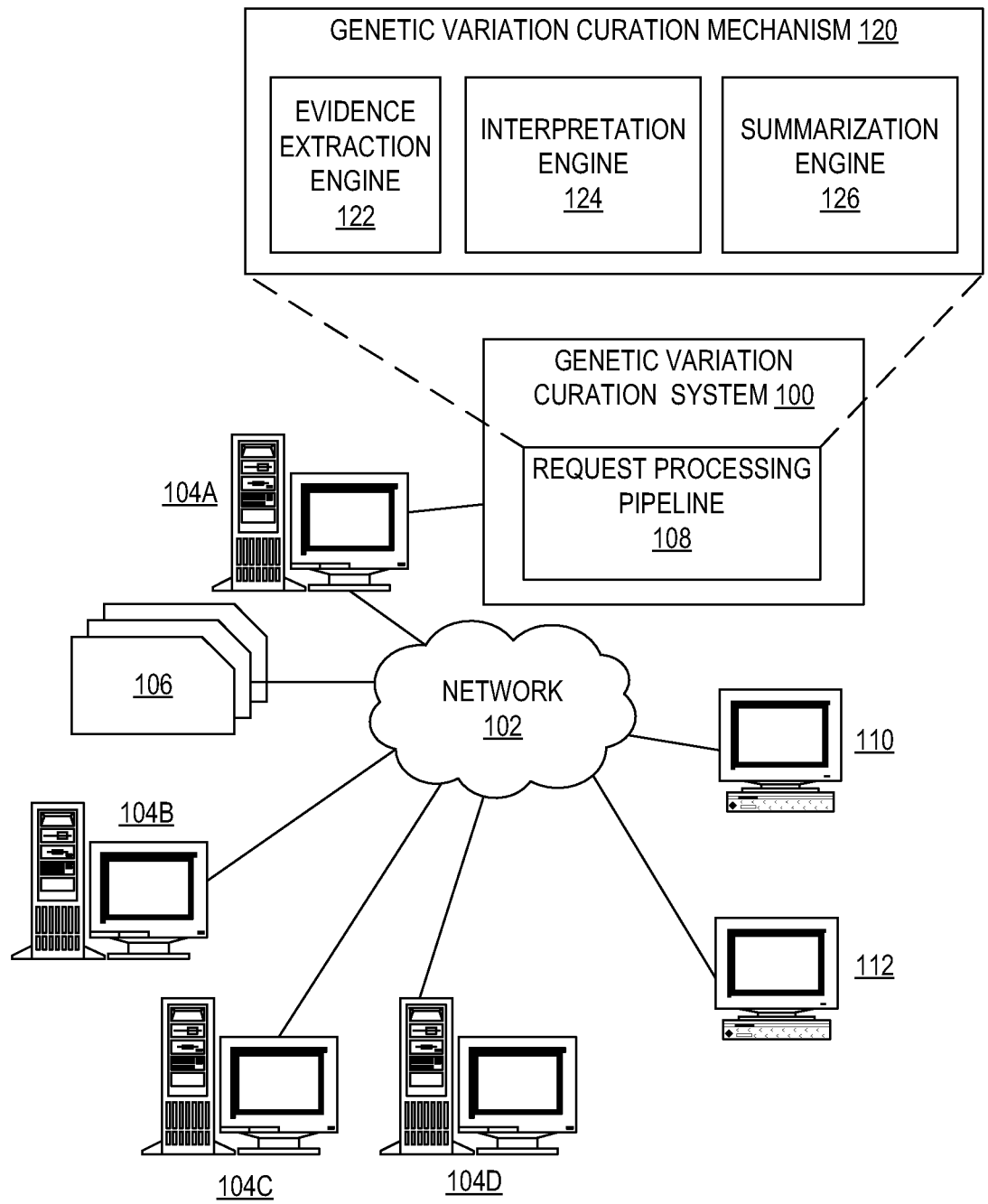
FIG. 1 depicts a schematic diagram of one illustrative embodiment of genetic variation curation system 100 implementing request processing pipeline 108 in computer network 102.

The presence of a genetic variant (a DNA change in a specific gene) may impact clinical care decisions. For example, the presence of genetic variants in tumors may predict sensitivity to drugs, determine the specific cancer type, suggest familial cancer predisposition, or the like. In order to determine whether a specific genetic variant is associated with disease, interpretation of available information on the genetic variant from multiple resources is required. This process is called variant curation and involves searching and processing of evidence from multiple resources, assessing the pathogenicity of the variant (classification) and writing a summary of the findings (variant annotation). The classification and summary are critical for the health care team in order to make informed clinical decisions. However, the number of resources and the scope of available evidence for each genetic variant may be exceedingly high and is continuously updated. Therefore, genetic variant curation poses a growing challenge on clinical teams.

Accordingly, the illustrative embodiments provide genetic variation curation mechanisms for automatically processing electronic files to identify genetic variants and automatically curating genetic variants from a multitude of sources using machine learning and natural language processing. Thus, the genetic variation curation mechanisms automatically extract and interpret evidence on genetic variants based on an input identifying a gene name. The genetic variation curation mechanisms may be trained to automatically extract and interpret evidence on genetic variants utilizing identifes of functional and non-functional labeled data. Once trained, the genetic variation curation mechanisms extract the evidence on genetic variants from publications, genomic databases, or the like. The genetic variation curation mechanisms may utilize focal entity detection to detect variant (Named Entity recognition) mentions in the text using a regular-expression based dictionary and subsequently identify focal genetic variants based on weighted scores from various sections. The genetic variation curation mechanisms may also use relation extraction to identify sentences expressing relation between the genetic variant and other entities such as medication, gene names, medical condition, effect on a medical condition, or the like, using relation extraction models, such as supervised such as supervised or distantly supervised binary classifiers. A supervised classifier would be trained on sentences labelled manually as positive/negative while a distantly supervised classifier would use some knowledge bank consisting of known relations between entities (gene, variant, drug condition) and then extract sentences expressing such relations from literature. One example of a sentence expressing relation between a gene-variant and a medication, and identified by the model may be "A patient with BRAF (L597S) mutant metastatic melanoma responded significantly to treatment with the MEK inhibitor, TAK-733." Another example of a sentence expressing relation between a gene-variant and a medication, and identified by the model may be "As mentioned previously, similar to cabozantinib, an overall response rate of 33% can be achieved with the use of single-agent BRAF inhibition (dabrafenib) in BRAF V600E-mutant lung cancers." The evidence on genetic variants, which may also be referred to as variant-specific information, extracted by the genetic variation curation mechanisms may include, but are not limited to:

A location of the genetic variant within a protein (domain).

A prevalence of the genetic variant in cancer.

A proximity of the genetic variant to splice sites. Based on this information a prediction may be made as to whether the genetic variant causes a splicing defect resulting in a pathogenic variant, Functional studies to determine an effect of the genetic variant on the function of the protein.

Reports associating the germline genetic variant with predisposition to cancer.

Reports associating the genetic variant as a diagnostic biomarker.

Reports associating the genetic variants as a drug response biomarker.

The genetic variation curation mechanisms then classify a genetic variant by its likelihood to be pathogenic and generate a summary of the findings (variant annotation). That is, for each document in the publications, genomic database, or the like, the genetic variation curation mechanisms perform a classification to identify functional studies publications using supervised classifiers. For each identified genetic variant, the genetic variation curation mechanisms classify all documents for the genetic variant subjected to supervised classifiers to identify variant as pathogenic, a variant of unknown significance, or benign. The genetic variation curation mechanisms may utilize one or more mechanism to determine the assigned classification, such as voting, weighted scoring, probability score from predictive model, or the like.

In determining the assigned classification, the genetic variation curation mechanisms utilize predicted splicing site information as genetic variants near the splicing site (intron-exon boundary) are more deleterious. In one embodiment, the genetic variation curation mechanisms utilize an algorithm that predicts whether the mutation is within 2 base pairs of intron-exon junction by looking at either DNA change (C. nomenclature) or Protein change (P. nomenclature). The algorithm may use any reference genome thus any transcript, which may then be expanded to multiple species and not just humans. The algorithm may also be extended to include a classifier that generates a splicing score based on external databases and software to predict splicing effects.

The genetic variation curation mechanisms then uses natural language processing to automatically summarize all documents for the genetic variant identifying all facts and relations expressed in the documents by extracting relevant portions of the document and generating a summary than annotates the origin of each fact. That is, the genetic variation curation mechanisms identify how likely an identified genetic variant is to cause or not cause the disease. Since the publications, genomic databases, or the like, that are used to identify the evidence on genetic variants, the genetic variation curation mechanisms continuously scan the publications, genomic databases, or the like, for new evidence on genetic variants and generate new summaries each time a genetic variant is identified as likely being pathogenic.

Before beginning the discussion of the various aspects of the illustrative embodiments and the improved computer operations performed by the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on hardware to thereby configure the hardware to implement the specialized functionality of the present invention which the hardware would not otherwise be able to perform, software instructions stored on a medium such that the instructions are readily executable by hardware to thereby specifically configure the hardware to perform the recited functionality and specific computer operations described herein, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

As noted above, the present invention provides mechanisms for automatically processing electronic files to identify genetic variants and automatically curating genetic variants from a multitude of sources using machine learning and natural language processing. That is, the genetic variation curation mechanisms automatically extract and interpret evidence on genetic variants based on an input identifying a gene name. The genetic variation curation mechanisms then classify a genetic variant by its likelihood to be pathogenic and generate a summary of the findings (variant annotation). The genetic variation curation mechanisms then uses natural language processing to automatically summarize all documents for the genetic variant identifying all facts and relations expressed in the documents by extracting relevant portions of the document and generating a summary than annotates the origin of each fact.

Figure 2:
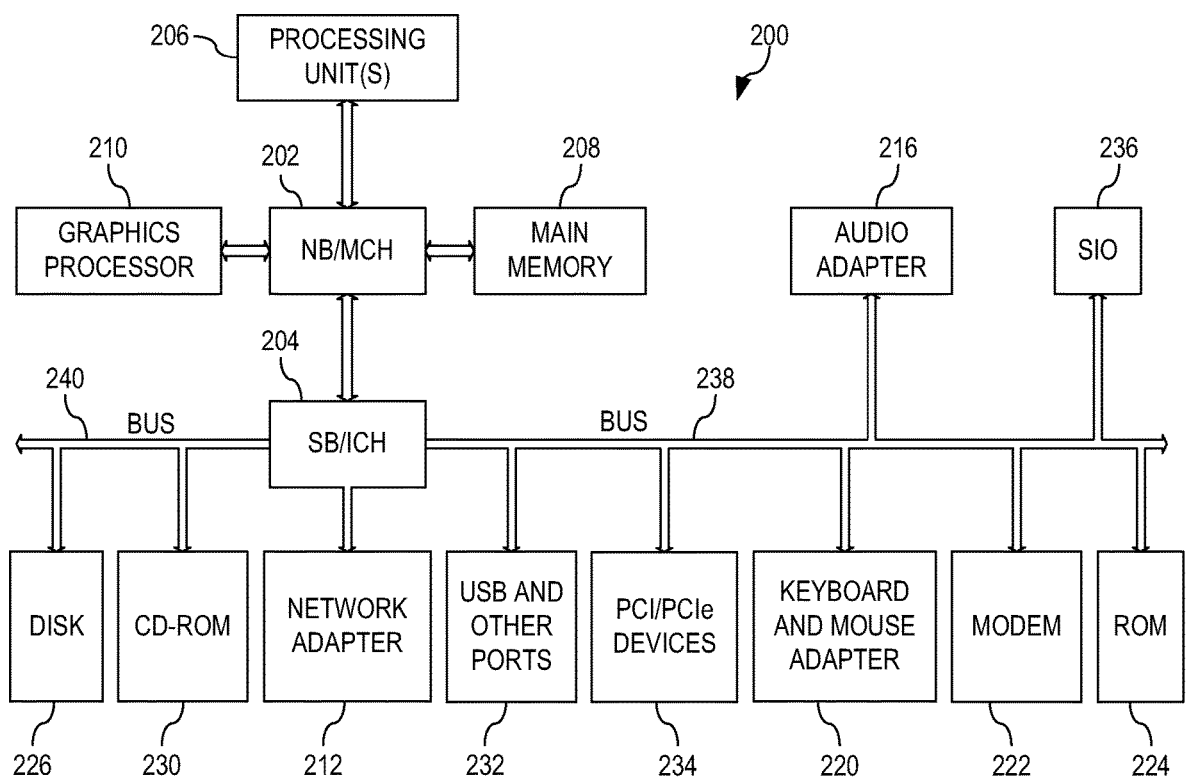
FIG. 2 is a block diagram of an example data processing system in which aspects of the illustrative embodiments are implemented.
Figure 3:
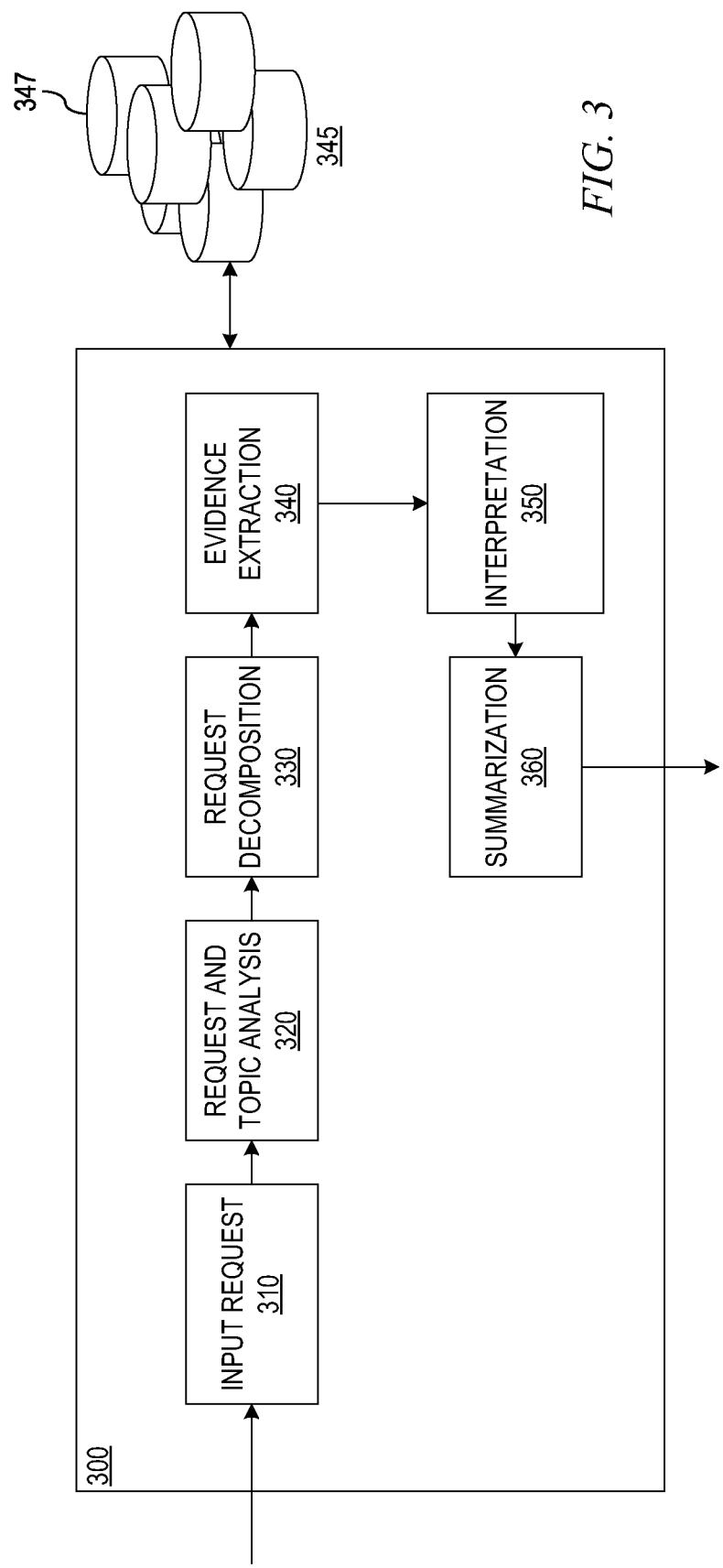
FIG. 3 illustrates an example of a genetic variation curation system processing pipeline which, in the depicted example, is a request processing pipeline used to process an input request in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing one example of a machine learning system, which is referred to as a genetic variation curation system herein, for automatically processing electronic files to identify genetic variants and automatically curating genetic variants from a multitude of sources using machine learning and natural language processing. The genetic variation curation system implements a request processing pipeline, request processing methodology, and request processing computer program product with which the mechanisms of the illustrative embodiments are implemented. These requests may be provided as structure or unstructured request messages, natural language requests, or any other suitable format for requesting an operation to be performed by the cognitive system. As described in more detail hereafter, the particular application that is implemented in the genetic variation curation system of the present invention is an application for determining Whether a specific genetic variant is associated with disease. It should be appreciated that the genetic variation curation system, while shown as having a single request processing pipeline in the examples hereafter, may in fact have multiple request processing pipelines. Each request processing pipeline may be separately trained and/or configured to process requests associated with different domains or be configured to perform the same or different analysis on input requests, depending on the desired implementation. For example, in some cases, a first request processing pipeline may be trained to operate on input requests directed to determine whether a specific genetic variant is associated with disease. In other cases, for example, the request processing pipelines may be configured to provide different types of cognitive functions or support different types of applications, such as one request processing pipeline being used for automatically curating genetic variants from a multitude of sources.

Moreover, each request processing pipeline may have its own associated corpus or corpora that they ingest and operate on, e.g., one corpus for gene information documents and another corpus for disease information related documents in the above examples. In some cases, the request processing pipelines may each operate on the same domain of input requests but may have different configurations, e.g., different annotators or differently trained annotators, such that different analysis and potential results are generated. The genetic variation curation system may provide additional logic for routing input requests to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a request pipeline. The description of example embodiments of the present invention hereafter will utilize a request pipeline as an example of a request processing pipeline that may be augmented to include mechanisms in accordance with one or more illustrative embodiments. It should be appreciated that while the present invention will be described in the context of the genetic variation curation system implementing one or more request pipelines that operate on an input request, the illustrative embodiments are not limited to such. Rather, the mechanisms of the illustrative embodiments may operate on requests that are not posed as "questions" but are formatted as requests for the genetic variation curation system to perform cognitive operations on a specified set of input data using the associated corpus or corpora and the specific configuration information used to configure the cognitive system. For example, rather than asking a natural language question of "What genetic variants are there for gene A?", the genetic variation curation system may instead receive a request of "Identify genetic variants for gene A," or the like. It should be appreciated that the mechanisms of the request pipeline may operate on requests in a similar manner to that of input natural language requests with minor modifications. In fact, in some cases, a request may be converted to a natural language request for processing by the request pipelines if desired for the particular implementation.

As will be discussed in greater detail hereafter, the illustrative embodiments may be integrated in, augment, and extend the functionality of these request processing pipeline with regard to automatically processing electronic files to identify genetic variants and automatically curating genetic variants from a multitude of sources using machine learning and natural language processing.

Thus, it is important to first have an understanding of how cognitive systems, i.e. a genetic variation curation system, implementing a request pipeline is implemented before describing how the mechanisms of the illustrative embodiments are integrated in and augment such genetic variation curation systems and request processing pipeline mechanisms. It should be appreciated that the mechanisms described in FIGS. 1-3 are only examples and are not intended to state or imply any limitation with regard to the type of genetic variation curation systems with which the illustrative embodiments are implemented. Many modifications to the example genetic variation curation system shown in FIGS. 1-3 may be implemented in various embodiments of the present invention without departing from the spirit and scope of the present invention.

As an overview, a genetic variation curation system is a specialized computer system, or set of computer systems, configured with hardware and/or software logic (in combination with hardware logic upon which the software executes) to emulate human cognitive functions. These genetic variation curation systems apply human-like characteristics to conveying and manipulating ideas which, when combined with the inherent strengths of digital computing, solve problems with high accuracy and resilience on a large scale. A genetic variation curation system performs one or more computer-implemented cognitive operations that approximate a human thought process as well as enable people and machines to interact in a more natural manner so as to extend and magnify human expertise and cognition. A genetic variation curation system comprises artificial intelligence logic, such as natural language processing (NLP) based logic, for example, and machine learning logic, which may be provided as specialized hardware, software executed on hardware, or any combination of specialized hardware and software executed on hardware. The logic of the genetic variation curation system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding.
Ingest and process vast amounts of structured and unstructured data.
Generate and evaluate hypothesis.
Weigh and evaluate responses that are based only on relevant evidence.
Provide situation-specific advice, insights, and guidance.
Improve knowledge and learn with each iteration and interaction through machine learning processes.
Enable decision making at the point of impact (contextual guidance).
Scale in proportion to the task.
Extend and magnify human expertise and cognition.
Identify resonating, human-like attributes and traits from natural language.
Deduce various language specific or agnostic attributes from natural language.
High degree of relevant recollection from data points (images, text, voice) (memorization and recall),
Predict and sense with situational awareness that mimic human cognition based on experiences,
Addressing requests based on natural language and specific evidence.

In one aspect, genetic variation curation systems provide mechanisms for addressing requests posed to these cognitive systems using a request processing pipeline or system and/or process requests which may or may not be posed as natural language requests. The request processing pipeline or system is an artificial intelligence application executing on data processing hardware that addresses requests pertaining to a given subject-matter domain presented in natural language. The request processing pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the request processing pipeline. The document may include any file, text, article, or source of data for use in the genetic variation curation system. For example, a genetic variation curation system pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input requests to cognitive system which implements the request processing pipeline. The request processing pipeline then provides results to the input request using the content in the corpus of data by evaluating documents, sections of documents, portions of data in the cot pus, or the like. When a process evaluates a given section of a document for semantic content, the process can use a variety of conventions to query such document from the request processing pipeline, e.g., sending the query to the request processing pipeline as a well-formed request which is then interpreted by the request processing pipeline and a response is provided containing one or more results to the input request. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the request processing pipeline receives an input request, parses the input request to extract the major features of the input request, uses the extracted features to formulate queries, and then applies those queries to the corpus of data. Based on the application of the queries to the corpus of data, the request processing pipeline generates a set of hypotheses, or candidate results to the input request, by looking across the corpus of data for portions of the corpus of data that have some potential for containing a valuable response to the input request. The request processing pipeline then performs deep analysis on the language of the input request and the language used in each of the portions of the corpus of data found during the application of the queries using a variety of reasoning algorithms. There may be hundreds or even thousands of reasoning algorithms applied, each of which performs different analysis, comparisons, natural language analysis, lexical analysis, or the like, and generates a score. For example, some reasoning algorithms may look at the matching of terms and synonyms within the language of the input request and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input request based on the specific area of focus of that reasoning algorithm. Each resulting score is then weighted against a statistical model. The statistical model captures how well the reasoning algorithm performed at establishing the inference between two similar passages for a particular domain during the training period of the request processing pipeline. The statistical model is used to summarize a level of confidence that the request processing pipeline has regarding the evidence that the potential response, i.e. candidate result, is inferred by the input request. This process is repeated for each of the candidate results until the request processing pipeline identifies candidate results that surface as being significantly stronger than others and thus, generates a final result, or ranked set of results, for the input request.

As mentioned above, request processing pipeline mechanisms operate by accessing information from a corpus of data or information (also referred to as a corpus of content), analyzing it, and then generating results based on the analysis of this data. Accessing information from a corpus of data typically includes: a database query that identifies results about what is in a collection of structured records, and a search that delivers a collection of document links in response to a query against a collection of unstructured data (text, markup language, etc.). Conventional cognitive systems are capable of generating results based on the corpus of data and the input request, verifying results to a collection of input requests for the corpus of data, correcting errors in digital text using a corpus of data, and selecting results to input requests from a pool of potential results, i.e. candidate results.

Content creators, such as article authors, electronic document creators, web page authors, document database creators, and the like, determine use cases for products, solutions, and services described in such content before writing their content. Consequently, the content creators know what results the content is intended to address in a particular topic addressed by the content. Categorizing the input requests, such as in terms of roles, type of information, tasks, or the like, associated with the input request, in each document of a corpus of data allows the request processing pipeline to more quickly and efficiently identify documents containing content related to a specific query. The content may also address other input requests that the content creator did not contemplate that may be useful to content users. The requests and results may be verified by the content creator to be contained in the content for a given document. These capabilities contribute to improved accuracy, system performance, machine learning, and confidence of the request processing pipeline. Content creators, automated tools, or the like, annotate or otherwise generate metadata for providing information useable by the request processing pipeline to identify these request and result attributes of the content.

Operating on such content, the request processing pipeline generates results for input requests using a plurality of intensive analysis mechanisms which evaluate the content to identify the most probable results, i.e. candidate results, for the input request. The most probable results are output as a ranked listing of candidate results ranked according to their relative scores or confidence measures calculated during evaluation of the candidate results, as a single final result having a highest ranking score or confidence measure, or which is a best match to the input request, or a combination of ranked listing and final result.

FIG. 1 depicts a schematic diagram of one illustrative embodiment of genetic variation curation system 100 implementing request processing pipeline 108 in computer network 102. For purposes of the present description, it will be assumed that request processing pipeline 108 is implemented as a genetic variation curation pipeline that operates on structured and/or unstructured requests in the form of input requests. Genetic variation curation system 100 is implemented on one or more computing devices 104A-D (comprising one or more processors and one or more memories, and potentially any other computing device elements generally known in the art including buses, storage devices, communication interfaces, and the like) connected to computer network 102. For purposes of illustration only, FIG. 1 depicts genetic variation curation system 100 being implemented on computing device 104A only, but as noted above genetic variation curation system 100 may be distributed across multiple computing devices, such as a plurality of computing devices 104A-D. Network 102 includes multiple computing devices 104A-D, which may operate as server computing devices, and computing devices 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, genetic variation curation system 100 and network 102 enables request processing and result generation functionality for one or more genetic variation curation system users via their respective computing devices 110-112. In other embodiments, genetic variation curation system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of genetic variation curation system 100 may be used with components, systems, sub-systems, and/or devices other than those that are depicted herein.

Genetic variation curation system 100 is configured to implement request processing pipeline 108 that receive inputs from various sources. The requests may be posed in the form of a natural language question, natural language request for information, natural language request for the performance of a cognitive operation, or the like. For example, genetic variation curation system 100 receives input from network 102, corpus or corpora of electronic documents 106, cognitive system users, and/or other data and other possible sources of input. In one embodiment, some or all of the inputs to genetic variation curation system 100 are routed through network 102. Various computing devices 104A-1) on network 102 include access points for content creators and cognitive system users. Some of computing devices 104A-1) include devices for a database storing corpus or corpora of data 106 (which is shown as a separate entity in FIG. 1 for illustrative purposes only). Portions of corpus or corpora of data 106 may also be provided on one or more other network attached storage devices, in one or more databases, or other computing devices not explicitly shown in FIG. 1. Network 102 includes local network connections and remote connections in various embodiments, such that genetic variation curation system 100 may operate in environments of any size, including local and global, e.g., the Internet.

In one embodiment, the content creator creates content in a document of corpus or corpora of data 106 for use as part of a corpus of data with genetic variation curation system 100. The document includes any file, text, article, or source of data for use in genetic variation curation system 100. Cognitive system users access genetic variation curation system 100 via a network connection or an Internet connection to network 102, and input requests to genetic variation curation system 100 that are processed based on the content in corpus or corpora of data 106. In one embodiment, the requests are formed using natural language. Genetic variation curation system 100 parses and interprets the request via request processing pipeline 108, and provides a result to the cognitive system user, e.g., genetic variation curation system user 110, containing one or more results to the input request posed, response to the request, results of processing the request, or the like. In some embodiments, genetic variation curation system 100 provides a response to users in a ranked list of candidate results while in other illustrative embodiments, genetic variation curation system 100 provides a single final result or a combination of a final result and ranked listing of other candidate results.

Genetic variation curation system 100 implements request processing pipeline 108 which comprises a plurality of stages for processing an input request based on information obtained from corpus or corpora of data 106. Request processing pipeline 108 generates results for the input request based on the processing of the input request and corpus or corpora of data 106. Request processing pipeline 108 will be described in greater detail hereafter with regard to FIG. 3.

In some illustrative embodiments, genetic variation curation system 100 may be the IBM Watson™ cognitive system available from International Business Machines Corporation of Armonk, New York, which is augmented with the mechanisms of the illustrative embodiments described hereafter. As outlined previously, a pipeline of the IBM Watson™ cognitive system receives an input request which it then parses to extract the major features of the request, which in turn are then used to formulate queries that are applied to corpus or corpora of data 106. Based on the application of the queries to corpus or corpora of data 106, a set of hypotheses, or candidate results to the input request, are generated by looking across corpus or corpora of data 106 for portions of corpus or corpora of data 106 (hereafter referred to simply as corpus 106) that have some potential for containing a valuable response to the input question/response (hereafter assumed to be an input question). Request processing Pipeline 108 of the IBM Watson™ cognitive system then performs deep analysis on the language of the input request and the language used in each of the portions of corpus 106 found during the application of the queries using a variety of reasoning algorithms.

The scores obtained from the various reasoning algorithms are then weighted against a statistical model that summarizes a level of confidence that request processing pipeline 108 of genetic variation curation system 100, in this example, has regarding the evidence that the potential candidate answer is inferred by the input request. This process is be repeated for each of the candidate results to generate ranked listing of candidate results which may then be presented to the user that submitted the input request, e.g., a user of client computing device 110, or from which a final result is selected and presented to the user.

As noted above, while the input to genetic variation curation system 100 from a client device may be posed in the form of a natural language request, the illustrative embodiments are not limited to such. Rather, the input request may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing gene information, disease information, and the like, to determine whether a specific variant is associated with disease.

In the context of the present invention, genetic variation curation system 100 may provide a cognitive functionality for automatically processing electronic files to identify genetic variants and automatically curating genetic variants from a multitude of sources using machine learning and natural language processing. For example, depending upon the particular implementation, the genetic variation curation systems based operations may comprise automatically extracting and interpreting evidence on genetic variants based on an input identifying a gene name. The genetic variation curation systems then classify a genetic variant by its likelihood to be pathogenic and generate a summary of the findings (variant annotation). In determining the assigned classification, the genetic variation curation systems utilize predicted splicing site information as genetic variants near the splicing site (intron-exon boundary) are more deleterious. In one embodiment, the genetic variation curation systems utilize an algorithm that predicts whether the mutation is within 2 base pairs of intron-exon junction by looking at either DNA change (C. nomenclature) or Protein change (P. nomenclature). The algorithm may use any reference genome thus any transcript, which may then be expanded to multiple species and not just humans. The algorithm may also be extended to include a classifier that generates a splicing score based on external databases and software to predict splicing effects. The genetic variation curation systems then uses natural language processing to automatically summarize all documents for the genetic variant identifying all facts and relations expressed in the documents by extracting relevant portions of the document and generating a summary than annotates the origin of each fact.

As shown in FIG. 1, the genetic variation curation system 100 is further augmented, in accordance with the mechanisms of the illustrative embodiments, to include logic implemented in specialized hardware, software executed on hardware, or any combination of specialized hardware and software executed on hardware, that trains a genetic variation curation mechanism 120 within request processing pipeline 108 to automatically processing electronic Ides to identify genetic variants and automatically curating genetic variants from a multitude of sources using machine learning and natural language processing.

Genetic variation curation mechanism 120 comprises evidence extraction engine 122 that analyzes multiple forms of evidence to extract evidence of genetic variants, the multiple form of evidence including, but are not limited to:
location of the genetic variant within a protein (domain).
A prevalence of the genetic variant in cancer.
A proximity of the genetic variant to splice sites. Based on this information a prediction may be made as to whether the genetic variant causes a splicing defect resulting in a pathogenic variant.
Functional studies to determine an effect of the genetic variant on the function of the protein.
Reports associating the germline genetic variant with predisposition to cancer.
Reports associating the genetic variant as a diagnostic biomarker.
Reports associating the genetic variants as a drug response biomarker.

Evidence extraction engine 122 extracts the evidence of genetic variants based on machine-learning classifiers such as named entity recognizers, relation extraction, natural language processing scores, or the like. With regard to named entity recognition, evidence extraction engine 122 utilizes focal entity detection to detect variant (Named Entity recognition) mentions in the text using a regular-expression based dictionary and subsequently identify focal genetic variants based on weighted scores from various sections. With regard to relation extraction, evidence extraction engine 122 may identify sentences expressing relation between the genetic variant and other entities such as medication, gene names, medical condition, effect on a medical condition, or the like, using relation extraction models, such as supervised such as supervised or distantly supervised binary classifiers. A supervised classifier would be trained on sentences labelled manually as positive/negative while a distantly supervised classifier would use some knowledge bank consisting of known relations between entities (gene, variant, drug condition) and then extract sentences expressing such relations from literature. One example of a sentence expressing relation between a gene-variant and a medication, and identified by the model may be "A patient with BRAF(L597S) mutant metastatic melanoma responded significantly to treatment with the MEK inhibitor, TAK-733." Another example of a sentence expressing relation between a gene-variant and a medication, and identified by the model may be "As mentioned previously, similar to cabozantinib, an overall response rate of 33% can be achieved with the use of single-agent BRAF inhibition (dabrafenib) in BRAF V600E-mutant lung cancers." Evidence extraction engine 122 may further use natural language processing (NLP) to generate natural language processing evidence scores for one or more portions of the evidence by adding evidence scores from each publication. That is, for each publication, evidence extraction engine 122 calculates an evidence score by multiplying number of times evidence is observed in the publication by a quality of literature. The quality of literature is derived by multiplying a number of times the evidence is cited with an impact factor of the publication. The impact factor of the publication may be identified by one or more of references to the publication by colleagues, citations of the publication in other articles, or the like. NLP evidence scores are utilized in ranking and sorting. Higher ranked variants are presented for subject matter review first. NLP evidence scores are refreshed every week as new publications are processed.

Genetic variation aeration mechanism 120 further comprises interpretation engine 124 that performs a pathogenticity assessment to classify each identified genetic variant by its likelihood to be pathogenic. That is, for each document in the publications, genomic databases, or the like, interpretation engine 124 performs a classification to identify functional studies publications using supervised classifiers. For each identified genetic variant, interpretation engine 124 classifies all documents for the genetic variant subjected to supervised classifiers to identify variant as pathogenic, a variant of unknown significance, or benign. Interpretation engine 124 may utilize one or more mechanism to determine the assigned classification, such as voting, weighted scoring, probability score from predictive model, or the like. Please provide at least one example of how the classification works.

In determining the assigned classification, interpretation engine 124 utilizes predicted splicing site information as genetic variants near the splicing site (intron-exon boundary) are more deleterious. In one embodiment, interpretation engine 124 utilizes an algorithm that predicts whether the mutation is within 2 base pairs of intron-exon junction by looking at either DNA change (C. nomenclature) or Protein change (P. nomenclature). The algorithm may use any reference genome thus any transcript, which may then be expanded to multiple species and not just humans. The algorithm may also be extended to include a classifier that generates a splicing score based on external databases and software to predict splicing effects.

Additionally, genetic variation curation mechanism 120 comprises summarization engine 126 that generates a summary of the findings (variant annotation). Summarization engine 126 uses natural language processing to automatically summarize all documents for the genetic variant identifying all facts and relations expressed in the documents by extracting relevant portions of the document and generates a summary than annotates the origin of each fact. That is, summarization engine 126 identifies how likely an identified genetic variant is to cause or not cause the disease. Summarization engine 126 automatically generates the summary by compiling the identified evidence into sentences. Below is an exemplary scheme utilized by summarization engine 126 for automatically generating of summary sentences.

The [variant] mutation is located within the [domain name] of the [gene name] protein.
The [variant] has been reported in [cancer type].
The [variant] is predicted to cause a splicing defect,
Functional studies have shown that [variant] results in altered [gene name] protein function (references),
The germline variant of this mutation has been identified in families affected with [associated disease](reference).
The [variant] is considered a diagnostic biomarker for [cancer type] (reference).
The [variant] is associated with sensitivity/resistance to [therapy name] (reference).
The [variant.] is therefore classified as [pathogenic/variant of unknown significance].

Since the publications, genomic databases, or the like, that are used to identify the evidence on genetic variants, genetic variation curation mechanism 120 continuously scan the publications, genomic databases, or the like, for new evidence on genetic variants and generate new summaries each time a genetic variant is identified as likely being pathogenic.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a genetic variation curation system 100 and request processing pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB ICH 204 through bus 238 and bus 240. PCI/PCIe devices may include, for example. Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 illustrates an example of a genetic variation curation system processing pipeline which, in the depicted example, is a request processing pipeline used to process an input request in accordance with one illustrative embodiment. As noted above, the genetic variation curation system with which the illustrative embodiments may be utilized are not limited to cognitive systems and thus, not limited to the use of a request processing pipeline. FIG. 3 is provided only as one example of the processing structure that may be implemented to process a natural language input requesting the operation of a genetic variation curation system to present a response or result to the natural language input.

The request processing pipeline of FIG. 3 may be implemented, for example, as request processing pipeline 108 of genetic variation curation system 100 in FIG. 1. It should be appreciated that the stages of the request processing pipeline shown in FIG. 3 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The request processing pipeline of FIG. 3 is augmented, for example, in one or more of the stages to implement the improved mechanism of the illustrative embodiments described hereafter, additional stages may be provided to implement the improved mechanism, or separate logic from request processing pipeline 300 may be provided for interfacing with request processing pipeline 300 and implementing the improved functionality and operations of the illustrative embodiments.

As shown in FIG. 3, request processing pipeline 300 comprises a plurality of stages 310-390 through which the cognitive system operates to analyze an input request and generate a final response or result. In an initial input request stage 310, the request processing pipeline 300 receives an input request that is presented in a natural language format. That is, a user inputs, via a user interface, an input request for which the user wishes to obtain an answer, e.g., "What genetic variants are there for gene A?", "Identify genetic variants for gene A.", or the like. In response to receiving the input request, the next stage of the request processing pipeline 300, i.e. the request and topic analysis stage 320, parses the input request using natural language processing (NLP) techniques to extract major features from the input question, and classify the major features according to types, e.g., names, dates, or any of a plethora of other defined topics. For example, in the example question above, the term "genetic variants" may be associated with a topic for "genes" indicating that the identity of a specific gene is being sought, "Gene A" may be identified as a proper name of a gene with which the question is associated, "variant" may be identified as a word indicative of proximity or relationship, and "genetics" may be indicative of a noun or other language topic.

In addition, the extracted major features include key words and phrases classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver," The focus of a question is the part of the question that, if replaced by the answer, makes the question a standalone statement. For example, in the question "What drug has been shown to relieve the symptoms of ADD with relatively few side effects?," the focus is "drug" since if this word were replaced with the answer, e.g., the answer "Adderall" can be used to replace the term "drug" to generate the sentence "Adderall has been shown to relieve the symptoms of ADD with relatively few side effects."The focus often, but not always, contains the LAT. On the other hand, in many' cases it is not possible to infer a meaningful LAT from the fetus.

Referring again to FIG. 3, the identified major features are then used during the request decomposition stage 330 to decompose the request into one or more queries that are applied to the corpora of data/information 345 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 345. That is, these various sources themselves, different collections of sources, and the like, represent a different corpus 347 within the corpora 345. There may be different corpora 347 defined for different collections of documents based on various criteria depending upon the particular implementation. For example, different corpora may be established for different topics, subject matter categories, sources of information, or the like. As one example, a first corpus may be associated with gene information while a second corpus may be associated with disease information. Alternatively, one corpus may be documents published by the Universal Protein Resource (UniProt) while another corpus may be Catalogue of Somatic Mutations in Cancer documents. Any collection of content having some similar attribute may be considered to be a corpus 347 within the corpora 345.

The queries are applied to one or more databases storing information about the electronic texts, documents, articles, websites, and the like, that make up the corpus of data/information, e.g., the corpus of data 106 in FIG. 1. The queries are applied to the corpus of data/information at the evidence extraction stage 340 to extract evidence of genetic variants for answering the input request, which may then be evaluated. That is, evidence extraction stage 340 analyzes multiple forms of evidence to extract evidence of genetic variants, the multiple form of evidence including, but are not limited to:

A location of the genetic variant within a protein (domain).

A prevalence of the genetic variant in cancer.

A proximity of the genetic variant to splice sites. Based on this information a prediction may be made as to whether the genetic variant causes a splicing defect resulting in a pathogenic variant.

Functional studies to determine an effect of the genetic variant on the function of the protein.

Reports associating the germline genetic variant with predisposition to cancer.

Reports associating the genetic variant as a diagnostic biomarker.

Reports associating the genetic variants as a drug response biomarker.

Evidence extraction stage 340 extracts the evidence of genetic variants based on machine-learning classifiers such as named entity recognizes, relation extraction, natural language processing scores, or the like. With regard to named entity recognition, evidence extraction stage 340 utilizes focal entity detection to detect variant (Named Entity recognition) mentions in the text using a regular-expression based dictionary and subsequently identify focal genetic variants based on weighted scores from various sections. With regard to relation extraction, evidence extraction stage 340 may identify sentences expressing relation between the genetic variant and other entities such as medication, gene names, medical condition, effect on a medical condition, or the like, using relation extraction models, such as supervised such as supervised or distantly supervised binary classifiers. A supervised classifier would be trained on sentences labelled manually as positive/negative while a distantly supervised classifier would use some knowledge bank consisting of known relations between entities (gene, variant, drug condition) and then extract sentences expressing such relations from literature One example of a sentence expressing relation between a gene-variant and a medication, and identified by the model may be "A patient with BRAF (L597S) mutant metastatic melanoma responded significantly to treatment with the MIX inhibitor, TAK-733." Another example of a sentence expressing relation between a gene-variant and a medication, and identified by the model may be "As mentioned previously, similar to cabozantinib, an overall response rate of 33% can be achieved with the use of single-agent BRAF inhibition (dabrafenib) in BRAF V600E-mutant lung cancers." Evidence extraction stage 340 may further use natural language processing (NLP) to generate natural language processing evidence scores for one or more portions of the evidence by adding evidence scores from each publication. That is, for each publication, evidence extraction stage 340 calculates an evidence score by multiplying number of times evidence is observed in the publication by a quality of literature. The quality of literature is derived by multiplying a number of times the evidence is cited with an impact factor of the publication. The impact factor of the publication may be identified by one or more of references to the publication by colleagues, citations of the publication in other articles, or the like. NTT evidence scores are utilized in ranking and sorting. Higher ranked variants are presented for subject matter review first. NLP evidence scores are refreshed every week as new publications are processed.

Request pipeline 300, in the interpretation stage 350, performs a pathogenicity assessment to classify each identified genetic variant by its likelihood to be pathogenic That is, for each document in the publications, genomic databases, or the like, interpretation stage 350 performs a classification to identify functional studies publications using supervised classifiers. For each identified genetic variant, interpretation stage 350 classifies all documents for the genetic variant subjected to supervised classifiers to identify variant as pathogenic, a variant of unknown significance, or benign. Interpretation stage 350 may utilize one or more mechanism to determine the assigned classification, such as voting, weighted scoring, probability score from predictive model, or the like. Please provide at least one example of how the classification works.

In determining the assigned classification interpretation stage 350 utilizes predicted splicing site information as genetic variants near the splicing site (intron-exon boundary) are more deleterious. In one embodiment, interpretation stage 350 utilizes an algorithm that predicts whether the mutation is within 2 base pairs of intron-exon junction by looking at either DNA change (C. nomenclature) or Protein change (P. nomenclature). The algorithm may use any reference genome thus any transcript, which may then be expanded to multiple species and not just humans. The algorithm may also be extended to include a classifier that generates a splicing score based on external databases and software to predict splicing effects.

Summarization stage 360 generates a summary of the findings (variant annotation). Summarization stage 360 uses natural language processing to automatically summarize all documents for the genetic variant identifying all facts and relations expressed in the documents by extracting relevant portions of the document and generates a summary than annotates the origin of each fact. That is, summarization stage 360 identifies how likely an identified genetic variant is to cause or not cause the disease. Summarization stage 360 automatically generates the summary by compiling the identified evidence into sentences. Below is an exemplary scheme utilized by summarization stage 360 for automatically generating of summary sentences.

The [variant] mutation is located within the [domain name] of the [gene name] protein.
The [variant] has been reported in [cancer type].
The [variant] is predicted to cause a splicing defect.
Functional studies have shown that [variant] results in altered [gene name] protein function (references).
The germline variant of this mutation has been identified in families affected with [associated disease](reference).
The [variant] is considered a diagnostic biomarker for [cancer type] (reference),
The [variant] is associated with sensitivity/resistance to [therapy name] (reference).
The [variant] is therefore classified as [pathogenic/variant of unknown significance], The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device, Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 4:
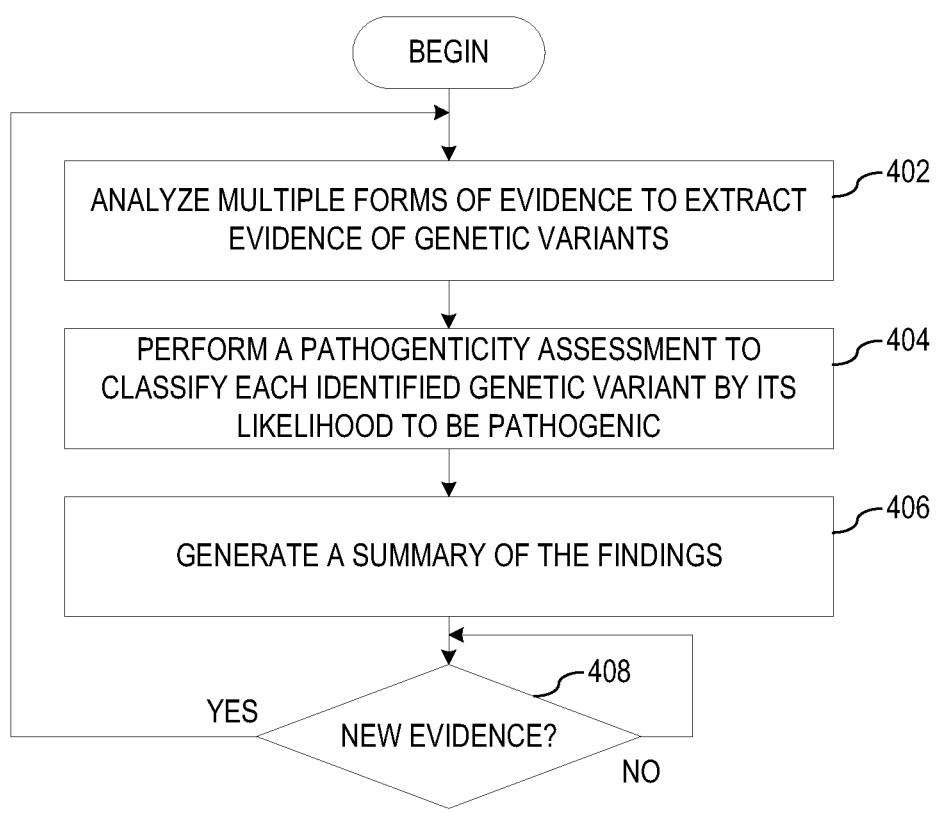
FIG. 4 depicts one example of the operations performed by a genetic variation curation system to automatically processing electronic files to identify genetic variants and automatically curating genetic variants from a multitude of sources using machine learning and natural language processing in accordance with an illustrative embodiment.

FIG. 4 depicts one example of the operations performed by a genetic variation curation system to automatically processing electronic files to identify genetic variants and automatically curating genetic variants from a multitude of sources using machine learning and natural language processing in accordance with an illustrative embodiment. As the operation begins, the genetic variation curation mechanism analyzes multiple forms of evidence to extract evidence of genetic variants (step 402), the multiple form of evidence including, but are not limited to:

A location of the genetic variant within a protein (domain).
A prevalence of the genetic variant in cancer.
A proximity of the genetic variant to splice sites. Based on this information a prediction may be made as to whether the genetic variant causes a splicing defect resulting in a pathogenic variant.
Functional studies to determine an effect of the genetic variant on the function of the protein.
Reports associating the germline genetic variant with predisposition to cancer.
Reports associating the genetic variant as a diagnostic biomarker.
Reports associating the genetic variants as a drug response biomarker.

The genetic variation curation mechanism extracts the evidence of genetic variants based on machine-learning classifiers such as named entity recognizers, relation extraction, natural language processing scores, or the like. With regard to named entity recognition, the genetic variation curation mechanism utilizes focal entity detection to detect variant (Named Entity recognition) mentions in the text using a regular-expression based dictionary and subsequently identify focal genetic variants based on weighted scores from various sections. With regard to relation extraction, the genetic variation curation mechanism may identify sentences expressing relation between the genetic variant and other entities such as medication, gene names, medical condition, effect on a medical condition, or the like, using relation extraction models, such as supervised such as supervised or distantly supervised binary classifiers. A supervised classifier would be trained on sentences labelled manually as positive/negative while a distantly supervised classifier would use some knowledge bank consisting of known relations between entities (gene, variant, drug condition) and then extract sentences expressing such relations from literature. One example of a sentence expressing relation between a gene-variant and a medication, and identified by the model may be "A patient with BRAF(L597S) mutant metastatic melanoma responded significantly to treatment with the MEK inhibitor, TAK-733." Another example of a sentence expressing relation between a gene-variant and a medication, and identified by the model may be "As mentioned previously, similar to cabozantinib, an overall response rate of 33% can be achieved with the use of single-agent BRAF inhibition (dabrafenib) in BRAF V600E-mutant lung cancers." The genetic variation curation mechanism may further use natural language processing (NLP) to generate natural language processing evidence scores for one or more portions of the evidence by adding evidence scores from each publication. That is, for each publication, evidence extraction engine 122 calculates an evidence score by multiplying number of times evidence is observed in the publication by a quality of literature. The quality of literature is derived by multiplying a number of times the evidence is cited with an impact factor of the publication. The impact factor of the publication may be identified by one or more of references to the publication by colleagues, citations of the publication in other articles, or the like. NLP evidence scores are utilized in ranking and sorting. Higher ranked variants are presented for subject matter review first. NLP evidence scores are refreshed every week as new publications are processed.

The genetic variation curation mechanism then performs a pathogenticity assessment to classify each identified genetic variant by its likelihood to be pathogenic (step 404). That is, for each document in the publications, genomic databases, or the like, the genetic variation curation mechanism performs a classification to identify functional studies publications using supervised classifiers. For each identified genetic variant, the genetic variation curation mechanism classifies all documents for the genetic variant subjected to supervised classifiers to identify variant as pathogenic, a variant of unknown significance, or benign. The genetic variation curation mechanism may utilize one or more mechanism to determine the assigned classification, such as voting, weighted scoring, probability score from predictive model, or the like. Please provide at least one example of how the classification works.

In determining the assigned classification, the genetic variation curation mechanism utilizes predicted splicing site information as genetic variants near the splicing site (intron-exon boundary) are more deleterious. In one embodiment, the genetic variation curation mechanism utilizes an algorithm that predicts whether the mutation is within 2 base pairs of intron-exon junction by looking at either DNA change (C. nomenclature) or Protein change (P. nomenclature). The algorithm may use any reference genome thus any transcript, which may then be expanded to multiple species and not just humans. The algorithm may also be extended to include a classifier that generates a splicing score based on external databases and software to predict splicing effects.

Additionally, the genetic variation curation mechanism generates a summary of the findings (variant annotation) (step 406). The genetic variation curation mechanism uses natural language processing to automatically summarize all documents for the genetic variant identifying all facts and relations expressed in the documents by extracting relevant portions of the document and generates a summary than annotates the origin of each fact. That is, the genetic variation curation mechanism identifies how likely an identified genetic variant is to cause or not cause the disease. The genetic variation curation mechanism automatically generates the summary by compiling the identified evidence into sentences. Below is an exemplary scheme utilized by the genetic variation curation mechanism for automatically generating of summary sentences.

The [variant] mutation is located within the [domain name] of the [gene name] protein.
The [variant] has been reported in [cancer type].
The [variant] is predicted to cause a splicing defect.
Functional studies have shown that [variant] results in altered [gene name] protein function (references).
The germline variant of this mutation has been identified in families affected with [associated disease](reference).
The [variant] is considered a diagnostic biomarker for [cancer type] (reference).
The [variant] is associated with sensitivity/resistance to [therapy name] (reference).
The [variant] is therefore classified as [pathogenic/variant of known significance].

Since the publications, genomic databases, or the like, that are used to identify the evidence on genetic variants, the genetic variation curation mechanism continuously scan the publications, genomic databases, or the like, for new evidence on genetic variants and generate new summaries each time a genetic variant is identified as likely being pathogenic. Thus, the genetic variation curation mechanism determines whether there is new evidence on genetic variants (step 408), if at step there is no new evidence, the operation returns to step 408. If at step 408 there is new evidence, the operation returns to step 402.

Figure 5:
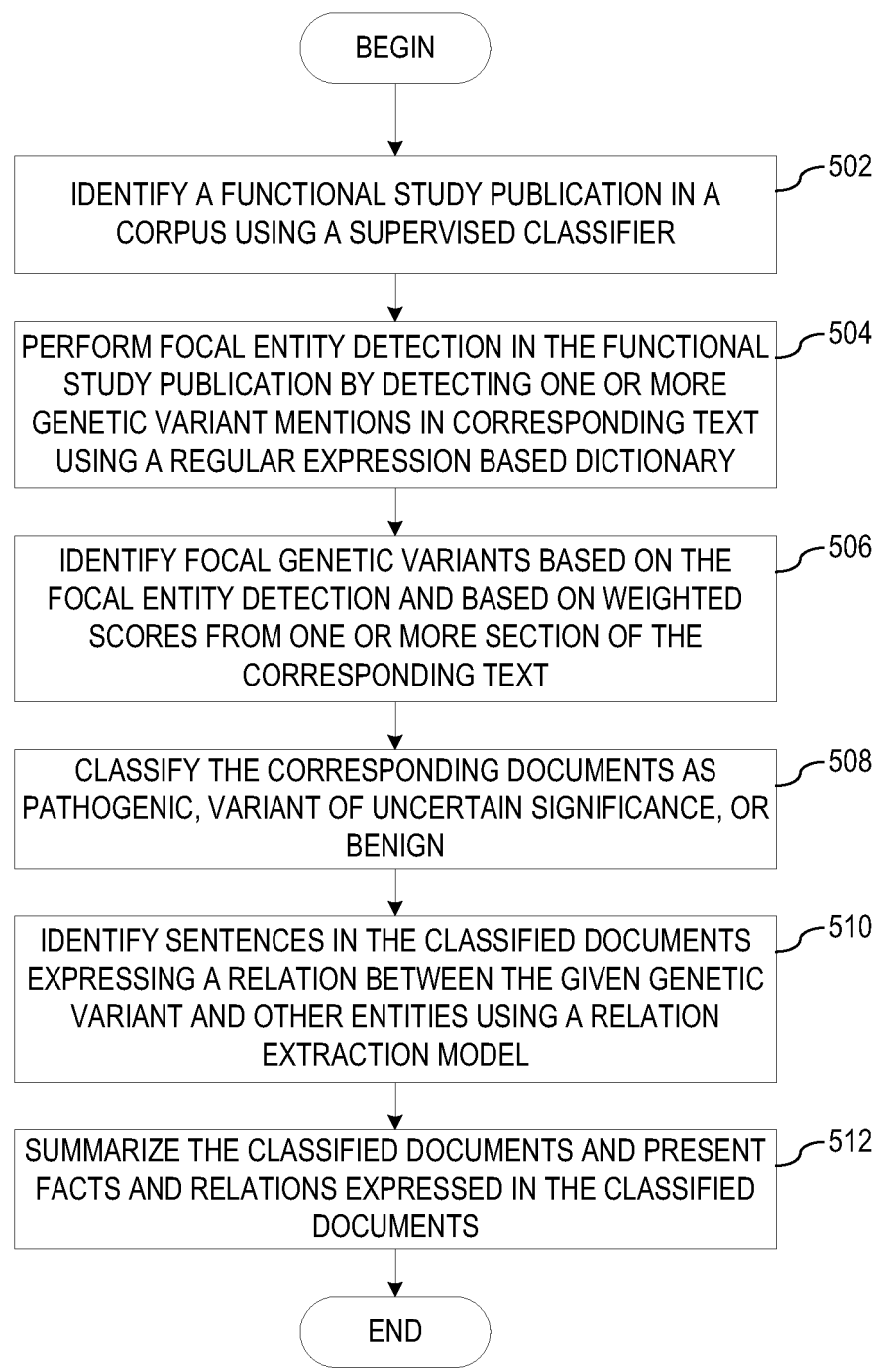
FIG. 5 depicts one example of the operations performed by a genetic variation curation system to automatically curating genetic variants from a multitude of sources using machine learning and natural language processing in accordance with an illustrative embodiment.

FIG. 5 depicts one example of the operations performed by a genetic variation curation system to automatically curating genetic variants from a multitude of sources using machine learning and natural language processing in accordance with an illustrative embodiment. As the operation begins, the genetic variation curation system identifies a functional study publication in a corpus using a supervised classifier (step 502). The genetic variation curation system performs focal entity detection in the functional study publication by detecting one or more genetic variant mentions in corresponding text using a regular expression based dictionary (step 504). The genetic variation curation system identifies focal genetic variants based on the focal entity detection and based on weighted scores from one or more section of the corresponding text (step 506).

For a given identified focal genetic variant, the genetic variation curation system classifies the corresponding documents as pathogenic, variant of uncertain significance, or benign (step 508). The genetic variation curation system identifies sentences in the classified documents expressing a relation between the given genetic variant and other entities using a relation extraction model (step 510). The genetic variation curation system then summarizes the classified documents and presents facts and relations expressed in the classified documents (step 512). The operation ends thereafter.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide mechanisms for automatically processing electronic files to identify genetic variants and automatically curating genetic variants from a multitude of sources using machine learning and natural language processing. Thus, the genetic variation curation mechanisms automatically extract and interpret evidence on genetic variants based on an input identifying a gene name. The genetic variation curation mechanisms may be trained to automatically extract and interpret evidence on genetic variants utilizing identifies of functional and non-functional labeled data. Once trained, the genetic variation curation mechanisms extract the evidence on genetic variants from publications, genomic databases, or the like. The genetic variation curation mechanisms may utilize focal entity detection to detect variant (Named Entity recognition) mentions in the text using a regular-expression based dictionary and subsequently identify focal genetic variants based on weighted scores from various sections. The genetic variation curation mechanisms may also use relation extraction to identify sentences expressing relation between the genetic variant and other entities such as medication, gene names, medical condition, effect on a medical condition, or the like, using relation extraction models, such as supervised such as supervised or distantly supervised binary classifiers. A supervised classifier would be trained on sentences labelled manually as positive/negative while a distantly supervised classifier would use some knowledge bank consisting of known relations between entities (gene, variant, drug condition) and then extract sentences expressing such relations from literature. One example of a sentence expressing relation between a gene-variant and a medication, and identified by the model may be "A patient with BRAF (L597S) mutant metastatic melanoma responded significantly to treatment with the MEK inhibitor, TAK-733." Another example of a sentence expressing relation between a gene-variant and a medication, and identified by the model may be "As mentioned previously, similar to cabozantinib, an overall response rate of 33% can be achieved with the use of single-agent BRAF inhibition (dabrafenib) in BRAT V600E-mutant lung cancers." The evidence on genetic variants, which may also be referred to as variant-specific information, extracted by the genetic variation curation mechanisms may include, but are not limited to:

A location of the genetic variant within a protein (domain).

A prevalence of the genetic variant in cancer.

A proximity of the genetic variant to splice sites. Based on this information a prediction may be made as to whether the genetic variant causes a splicing defect resulting in a pathogenic variant.

Functional studies to determine an effect of the genetic variant on the function of the protein.

Reports associating the germline genetic variant with predisposition to cancer.

Reports associating the genetic variant as a diagnostic biomarker.

Reports associating the genetic variants as a drug response biomarker.

The genetic variation curation mechanisms then classify a genetic variant by its likelihood to be pathogenic and generate a summary of the findings (variant annotation). That is, for each document in the publications, genomic database, or the like, the genetic variation curation mechanisms perform a classification to identify functional studies publications using supervised classifiers. For each identified genetic variant, the genetic variation curation mechanisms classify all documents for the genetic variant subjected to supervised classifiers to identify variant as pathogenic, a variant of unknown significance, or benign. The genetic variation curation mechanisms may utilize one or more mechanism to determine the assigned classification, such as voting, weighted scoring, probability score from predictive model, or the like.

In determining the assigned classification, the genetic variation curation mechanisms utilize predicted splicing site information as genetic variants near the splicing site (intron-exon boundary) are more deleterious. In one embodiment, the genetic variation curation mechanisms utilize an algorithm that predicts whether the mutation is within 2 base pairs of intron-exon junction by looking at either DNA change (C. nomenclature) or Protein change (P. nomenclature). The algorithm may use any reference genome thus any transcript, which may then be expanded to multiple species and not just humans. The algorithm may also be extended to include a classifier that generates a splicing score based on external databases and software to predict splicing effects.

The genetic variation curation mechanisms then uses natural language processing to automatically summarize all documents for the genetic variant identifying all facts and relations expressed in the documents by extracting relevant portions of the document and generating a summary than annotates the origin of each fact. That is, the genetic variation curation mechanisms identify how likely an identified genetic variant is to cause or not cause the disease. Since the publications, genomic databases, or the like, that are used to identify the evidence on genetic variants, the genetic variation curation mechanisms continuously scan the publications, genomic databases, or the like, for new evidence on genetic variants and generate new summaries each time a genetic variant is identified as likely being pathogenic.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system, for processing electronic documents to identify genetic variants of a gene, the method comprising:

executing a first computer-implemented machine learning training of a first machine learning computer model based on a first labeled training dataset to train the first machine learning computer model to detect genetic variant mentions in natural language text of first electronic documents using a regular expression dictionary and focal genetic variant identification, to thereby generate a first trained machine learning computer model;

executing a second computer-implemented machine learning training of a second machine learning computer model based on a second labeled training dataset to train the second machine learning computer model to extract relations between genetic variants and other entities from the natural language text of the first electronic documents based on a knowledge bank of known relations between entities, to thereby generate a second trained machine learning computer model;

extracting evidence of one or more genetic variants of the gene and corresponding information from second electronic documents in a corpus of information, at least by executing the first trained machine learning computer model and the second trained machine learning computer model on the second electronic documents, wherein the evidence comprises genetic variant mentions and genetic variant relations for corresponding ones of the one or more genetic variants;

classifying each genetic variant of the one or more genetic variants based on whether the genetic variant is identified as being pathogenic in the evidence of the one or more genetic variants at least by executing an algorithm that predicts whether the genetic variant is within a predetermined distance of a splicing site; and performing genetic variant annotation to generate a summary at least by extracting portions of the plurality of documents corresponding to the genetic variant mentions of the one or more genetic variants and genetic variant relations and executing natural language processing on the identified portions to generate the summary.

2. The method of claim 1, wherein the evidence extracted by the execution of the first trained machine learning computer model and second machine learning computer model on the second electronic documents comprises one or more of:

a location of the one or more genetic variants within a protein, a prevalence of the one or more genetic variants in cancer, a proximity of the one or more genetic variants to splice sites, a functional study to determine an effect of the one or more genetic variants on a function of the protein, a report associating the one or more genetic variants with predisposition to cancer, a report associating the one or more genetic variants as a diagnostic biomarker, or a report associating the one or more genetic variants as a drug response biomarker.

3. The method of claim 1, wherein classifying each genetic variant of the one or more genetic variants based on whether the genetic variant is identified as being pathogenic comprises:

for each of the one or more genetic variants, classifying documents for the one or more genetic variants as either pathogenic, a variant of uncertain significance, or benign.

4. The method of claim 1, wherein the predetermined distance of the splicing site comprises a distance of within 2 base pairs of an intron-exon junction, and wherein the distance is deterred based on a DNA change or protein change.

5. The method of claim 1, wherein extracting evidence of one or more genetic variants of the gene and corresponding information from second electronic documents further comprises generating an evidence score based on a quality of each second electronic document, wherein the quality of each second electronic document is based on an impact factor of the second electronic document.

6. The method of claim 5, wherein the evidence score is generated based on a multiplication of a number of times the evidence is cited with an impact factor of the second electronic document.

7. The method of claim 1, wherein performing genetic variant annotation to generate the summary comprises inserting portions of the evidence into fields of predefined natural language sentences to generate a natural language summary.

8. A computer program product comprising a computer readable storage medium having a computer readable program for processing electronic documents to identify genetic variants of a gene stored therein, wherein the computer readable program, when executed on a computing device, causes the computing device to:

execute a first computer-implemented machine learning training of a first machine learning computer model based on a first labeled training dataset to train the first machine learning computer model to detect genetic variant mentions in natural language text of first electronic documents using a regular expression dictionary and focal genetic variant identification, to thereby generate a first trained machine learning computer model;

execute a second computer-implemented machine learning training of a second machine learning computer model based on a second labeled training dataset to train the second machine learning computer model to extract relations between genetic variants and other entities from the natural language text of the first electronic documents based on a knowledge bank of known relations between entities, to thereby generate a second trained machine learning computer model;

extract evidence of one or more genetic variants of the gene and corresponding information from second electronic documents in a corpus of information, at least by executing the first trained machine learning computer model and the second trained machine learning computer model on the second electronic documents, wherein the evidence comprises genetic variant mentions and genetic variant relations for corresponding ones of the one or more genetic variants;

classify each genetic variant of the one or more genetic variants based on whether the genetic variant is identified as being pathogenic in the evidence of the one or more genetic variants at least by executing an algorithm that predicts whether the genetic variant is within a predetermined distance of a splicing site; and perform genetic variant annotation to generate a summary at least by extracting portions of the plurality of documents corresponding to the genetic variant mentions of the one or more genetic variants and genetic variant relations and executing natural language processing on the identified portions to generate the summary.

9. The computer program product of claim 8, wherein the evidence extracted by the execution of the first trained machine learning computer model and second machine learning computer model on the second electronic documents comprises one or more of:
   a location of the one or more genetic variants within a protein,
   a prevalence of the one or more genetic variants in cancer,
   a proximity of the one or more genetic variants to splice sites,
   a functional study to determine an effect of the one or more genetic variants on a function of the protein,
   a report associating the one or more genetic variants with predisposition to cancer,
   a report associating the one or more genetic variants as a diagnostic biomarker, or
   a report associating the one or more genetic variants as a drug response biomarker.

10. The computer program product of claim 8, wherein the computer readable program to classify each genetic variant of the one or more genetic variants based on whether the genetic variant is identified as being pathogenic further causes the computing device to:
   for each of the one or more genetic variants, classify documents for the one or more genetic variants as either pathogenic, a variant of uncertain significance, or benign.

11. The computer program product of claim 8, wherein the predetermined distance of the splicing site comprises a distance of within 2 base pairs of an intron-exon junction, and wherein the distance is deterred based on a DNA change or protein change.

12. The computer program product of claim 8, wherein extracting evidence of one or more genetic variants of the gene and corresponding information from second electronic documents further comprises generating an evidence score based on a quality of each second electronic document, wherein the quality of each second electronic document is based on an impact factor of the second electronic document.

13. The computer program product of claim 12, wherein the evidence score is generated based on a multiplication of a number of times the evidence is cited with an impact factor of the second electronic document.

14. The computer program product of claim 8, wherein performing genetic variant annotation to generate the summary comprises inserting portions of the evidence into fields of predefined natural language sentences to generate a natural language summary.

15. An apparatus for processing electronic documents to identify genetic variants of a gene comprising:
   a processor; and
   a memory coupled to the processor, wherein the memory comprises instructions which, when executed by the processor, cause the processor to:
   execute a first computer-implemented machine learning training of a first machine learning computer model based on a first labeled training dataset to train the first machine learning computer model to detect genetic variant mentions in natural language text of first electronic documents using a regular expression dictionary and focal genetic variant identification, to thereby generate a first trained machine learning computer model;
   execute a second computer-implemented machine learning training of a second machine learning computer model based on a second labeled training dataset to train the second machine learning computer model to extract relations between genetic variants and other entities from the natural language text of the first electronic documents based on a knowledge bank of known relations between entities, to thereby generate a second trained machine learning computer model;
   extract evidence of one or more genetic variants of the gene and corresponding information from second electronic documents in a corpus of information, at least by executing the first trained machine learning computer model and the second trained machine learning computer model on the second electronic documents, wherein the evidence comprises genetic variant mentions and genetic variant relations for corresponding ones of the one or more genetic variants;
   classify each genetic variant of the one or more genetic variants based on whether the genetic variant is identified as being pathogenic in the evidence of the one or more genetic variants at least by executing an algorithm that predicts whether the genetic variant is within a predetermined distance of a splicing site; and
   perform genetic variant annotation to generate a summary at least by extracting portions of the plurality of documents corresponding to the genetic variant mentions of the one or more genetic variants and genetic variant relations and executing natural language processing on the identified portions to generate the summary.

16. The apparatus of claim 15, wherein the evidence extracted by the execution of the first trained machine learning computer model and second machine learning computer model on the second electronic documents comprises one or more of:
   a location of the one or more genetic variants within a protein,
   a prevalence of the one or more genetic variants in cancer,
   a proximity of the one or more genetic variants to splice sites,
   a functional study to determine an effect of the one or more genetic variants on a function of the protein,
   a report associating the one or more genetic variants with predisposition to cancer,
   a report associating the one or more genetic variants as a diagnostic biomarker, or
   a report associating the one or more genetic variants as a drug response biomarker.

17. The apparatus of claim 15, wherein the predetermined distance of the splicing site comprises a distance of within 2 base pairs of an intron-exon junction, and wherein the distance is deterred based on a DNA change or protein change.

18. The apparatus of claim 15, wherein extracting evidence of one or more genetic variants of the gene and corresponding information from second electronic documents further comprises generating an evidence score based on a quality of each second electronic document, wherein the quality of each second electronic document is based on an impact factor of the second electronic document.

19. The apparatus of claim 18, wherein the evidence score is generated based on a multiplication of a number of times the evidence is cited with an impact factor of the second electronic document.

20. The apparatus of claim 15, wherein performing genetic variant annotation to generate the summary comprises inserting portions of the evidence into fields of predefined natural language sentences to generate a natural language summary.

\* \* \* \* \*